United States Patent [19]
Ravich

[11] Patent Number: 5,811,817
[45] Date of Patent: Sep. 22, 1998

[54] METHOD & APPARATUS FOR DETECTING FRACTURE FILLED DIAMONDS

[76] Inventor: Gilbert Norman Ravich, 15613 S. Doty Ave., Lawndale, Calif. 90260

[21] Appl. No.: 919,763

[22] Filed: Aug. 28, 1997

Related U.S. Application Data

[63] Continuation-in-part of Ser. No. 641,011, Apr. 25, 1996, abandoned.

[51] Int. Cl.⁶ ............................ G01N 21/87; G01N 21/88; G01N 21/33
[52] U.S. Cl. ........................ 250/372; 250/373; 250/461.1; 356/30
[58] Field of Search ................................ 250/372, 358.1, 250/461.1, 373, 370.08; 356/30

[56] References Cited

U.S. PATENT DOCUMENTS

| | | | |
|---|---|---|---|
| 2,853,393 | 9/1958 | Beck et al. | 106/47 |
| 4,394,580 | 7/1983 | Gielisse | 250/461.1 |
| 4,504,114 | 3/1985 | Arrington | 250/372 |
| 5,536,943 | 7/1996 | Smith et al. | 250/372 |

FOREIGN PATENT DOCUMENTS

| | | | |
|---|---|---|---|
| 0345949 | 12/1989 | European Pat. Off. | G01N 21/62 |
| 2 528 580 | 12/1983 | France | 356/30 |
| 2275788 | 9/1994 | United Kingdom | G01N 21/87 |

OTHER PUBLICATIONS

Kammerung, et al., "An Update on Filled Diamonds: Identification and Durability"; Gems & Gemology Fall 1994.

Dumbaugh, "Heavy Metal Oxide Glasses Containing $Bi_2O_3$," vol. 27, No. 3; Jun. 1986 Physics and Chemistry of Glasses.

Chrenko, et al., "Physical Properties of Diamond" (AG.E. Paper); Oct. 1975.

*Primary Examiner*—Edward J. Glick
*Attorney, Agent, or Firm*—Gene Scott-Patent Law & Venture Group

[57] ABSTRACT

The detection of fractures in diamonds which are filled with high index of refraction glass is easily and quickly carried out by observation under ultra violet light. Such light having a wavelength between 300 and 400 nm, as reflected from, or transmitted through, such diamonds is imaged using a CCD camera, or directly by the use of fluorescent conversion to the visible spectrum. In either approach, the fracture fills are clearly and immediately distinguishable.

26 Claims, 5 Drawing Sheets

METHOD & APPARATUS FOR DETECTING FRACTURE FILLED DIAMONDS

This application is a continuation-in-part of prior filed application Ser. No.: 08/641,011, filed on: Apr. 25, 1996, now abandoned.

BACKGROUND OF THE INVENTION

1. Field of the Invention

This invention relates generally to the evaluation of gemstones, and more particularly to an improved method for viewing or otherwise imaging the fractures in a diamond, especially those that have been filled.

2. Description of Related Art

Many natural cut and polished diamonds can be enhanced in visual appearance by a variety of treatments. Fracture filling with high index glasses is one such method. An extensive review of fracture filled diamonds is covered by Robert C. Kammerling, Shane F. McClure, Mary L. Johnson, John I. Koivila, Thomas M. Moses, Emmanuel Fritsch, and James E. Shigley, see Gems & Gemology, Fall 1994. A fracture filled diamond's cosmetic appearance may be drastically improved with a major reduction in the visibility of natural fractures. In some cases the filling treatment can also lighten the color of the diamond. The first commercially available diamond fracture filling treatment was developed in the 1980's by Zvi Yehuda of Ramat Gan, Israel, see Gems & Gemology, Fall 1994. The technique involves cleaning, then filling the fractures with high index glasses, heating in a controlled furnace, cooling and then removing excess filling glass from the diamond's surface.

Fracture filling of diamonds has become very popular and its use is increasing. The attraction of fracture filling rests upon an improvement in the visual appearance, and hence, the implied increase in value. The majority of treated diamonds are one tenth carat or larger. The fracture filling method can result in an improvement in clarity of several grades. The technique involves the use of high index glasses. These glasses are made up of heavy metal oxides including those containing lead and bismuth. Please see, Heavy metal oxides glasses containing BiO, W. H. Dumbaught; Physics and chemistry of Glasses, Vol. 27, #3, Jun. 1988. See also, U.S. Pat. No. 2,853,393 Sept. 23, 1958. These high index glasses melt and flow at temperatures well under the burn point of diamond. The optical refractive index of lead and bismuth oxide (2.2–2.6) closely match that of diamond (2.41). When two transparent optical media having very similar indexes of refraction, are brought into contact, it becomes difficult to differentiate one material from the other. Rather, the media appear continuous. Both lead and bismuth oxides as glasses, have very high clarity. The use of diamond fracture filling procedures are not frowned upon. However, the misrepresentation of a diamond to be of a higher quality then it actually is, is fraudulent.

Current techniques to identify fracture filled diamonds involve careful microscopic examination by a trained observer. A variety of inspection procedures using various illuminating arrangements are implemented in an effort to highlight filled fractures if there are any. Currently the use of very intense single fiber illumination can reveal the possibility of a fracture filled diamond by careful orientation and examination for the flash affect, well known in this industry. The flash affect is the result of an imperfect match in the spectral dispersion of diamond and high index glasses. If the index of refraction for each wavelength or color of light is the same for both materials, then no dispersion will occur. However, the high index filling glasses appear to vary somewhat from that of diamond. This miss match generates flashes of various colors off the sharp edges of the filled fracture when it receives just the right amount of light. Even so, examination can at times be confused with the colors produced from the natural iridescence of an unfilled fracture. The examination of filled diamonds, or, more importantly, those that are expected to be filled, requires a highly trained observer and a very careful review.

Other relevant prior art includes: Stewart, European Patent Application, Publication Number 0 345 949 A2, teaches sorting of a diamond-bearing ore particles moving on a conveyor belt. Exciting radiation strikes the belt along an extended line. Diamonds are detected by passing the emitted radiation through a narrow band-pass filter and sensing the Raman radiation with a photo-multiplier tube. Only axial-parallel rays passing through the filter reach the photo-multiplier tube. An array of side-by-side converging lenses can be used; the lenses being of rectangular shape, so that radiation emitted by each particle is passed in parallel rays through a filter. In order to stop rays having an angle of incidence greater than the maximum permitted, to avoid identifying non-diamond material, a further converging lens is used to focus the rays at the plane of a telecentric stop. The stop, halts rays having too great an angle of incidence. The position of the diamond can be detected for instance by a CCD array or by a time domain technique. The apparatus can be monitored by giving a signal when the radiation from tracer stones and holes on either side of the belt, differ from predetermined values.

Spear, et al., UK Patent Application, GB 2 275 788 A, discloses a method and apparatus for distinguishing natural diamond from synthetic diamond by observing the luminescence by investigating the arrangement of growth sectors in the diamond. Beck, et al., U.S. Pat. No. 2,853,393, discloses transparent high-index glass elements, novel in composition and which have an extraordinarily high refractive index value (at least 2.1). The elements have refractive indices as high as, and higher than, that of diamonds i.e. higher than 2.4, including elements having refractive indices of 2.6 to 2.7. The glasses have high optical dispersion values. The glasses are stable to sunlight and to exposure to humid atmospheres and are not damaged by immersion in water.

General Electric, Chrenko, R. M., in his paper as part of the G. E. Technical Information Series, No. 75CRD089, dated October 1975, summarizes data on a wide variety of physical properties for both synthesized and natural diamond. Included are published and previously unpublished data, with much of the data being given in tables or graphs and illustrations. The text offers elaborations and explanations of some of the data and, in addition, some, but not all, of the cited data has been critically analyzed. Topics and properties covered are: growth, structure, types, impurities, optical, electrical, EPR, irradiation, thermal, and mechanical properties, including spectral response.

Kammerling, et al, provides "An Update on Filled Diamonds: Identification and Durability", as published in Gems & Gemology, 1994 Fall. This article describes the techniques used by three major diamond houses in improving the appearance of diamonds. Noted, is the fact that treated diamonds from all three firms were damaged by direct heating and by repolishing facets intersected by the filled breaks. Some stones were adversely affected by some standard cleaning procedures and wear conditions. Although lead-based glass filling materials may be detected by S-radiograph and EDXRF spectroscopy, as well as by certain internal features, it was found that flash effects were the most distinctive characteristic of fracture filling.

Dumbaugh, teaches: "Heavy metal oxide glasses containing Bi2O3" as published in, *Physics and Chemistry of Glasses*, Vol. 27 No. 3, 1986 June However, the prior art does not teach an easy to use; can be used by any novice after a short introduction and "show and tell", low cost method and apparatus which provides the capability of easily and quickly identifying diamonds that are filled. The prior art teaches complex methods and systems, i.e., spectroscopy, that requires very high skill and expensive apparatus. The present invention fulfills these needs and provides further related advantages as described in the following summary.

SUMMARY OF THE INVENTION

The present invention teaches that fracture filled diamonds may be visualized by the use of relatively simple ultra violet microscopy technique. It was found that diamond filling materials are revealed by their absorption of ultra violet light. We have discovered that when illuminated in transmission or internal reflection and viewed by an ultra violet transmitting microscope coupled to a CCD video camera sensitive to ultra violet light, filling materials are rendered visible. The magnified ultra violet diamond image may be displayed on a video monitor. We have discovered that high index heavy metal oxide glasses in diamond fractures, begin to absorb violet and near ultra violet light at 400 nm. At 365 nm the high index glasses have very strong absorption. Natural diamond, on the other hand, is highly transparent at these wavelengths. A low power microscope is utilized to view the diamonds. This microscope, however, is configured with ultra violet transmitting optics, an ultra violet light source and an ultra violet sensitive video camera. When a fracture filled diamond is placed in the field of view and the microscope is focused, those areas that have been filled with high index glasses appear dark against a lightened background of the transmitted, scattered, or internally reflected ultra violet light. The diamond may be viewed top face up or top face down. Thus, an object of the present invention is to provide a method and apparatus for directly visualizing fracture fillings in diamonds with an inexpensive and well known type of equipment.

Additionally, we have discovered that immersion liquids such as alfa mono bromonapthalene may be used to increase the light transmission into and out of the diamond. This procedure is easily implemented by placing the diamond in a ultra violet transparent cell and filling it with the immersion fluid. Thus it is another object of the present invention to provide a method, as above, that is able to increase the light transmission into and out of the diamonds so that visualization is enhanced, thus avoiding the necessity of a darkened room or other preparations.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention, an apparatus and method for using the apparatus, for detecting the presence of fracture filled portions on and in a diamond. In such drawings:

FIGS. 2–10 are schematic diagrams thereof, wherein;

DETAILED DESCRIPTION OF THE PREFERRED EMBODIMENT

The above described drawing figures illustrate an apparatus, and method for using the apparatus, for detecting the presence of fracture filled portions on and in a diamond and other gemstones.

Figure 1:
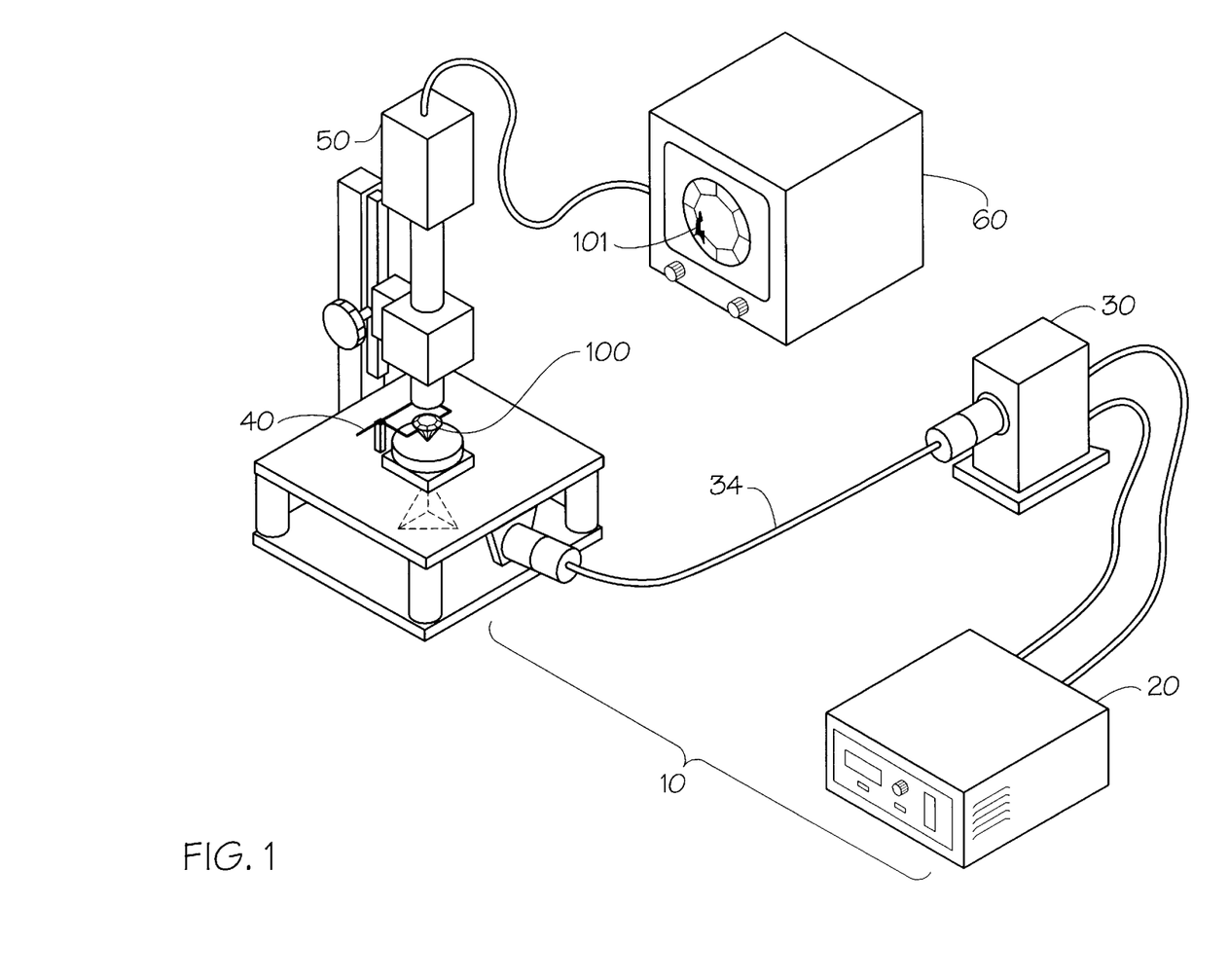
FIG. 1 is a perspective view of the preferred embodiment of the present invention.
Figure 2:
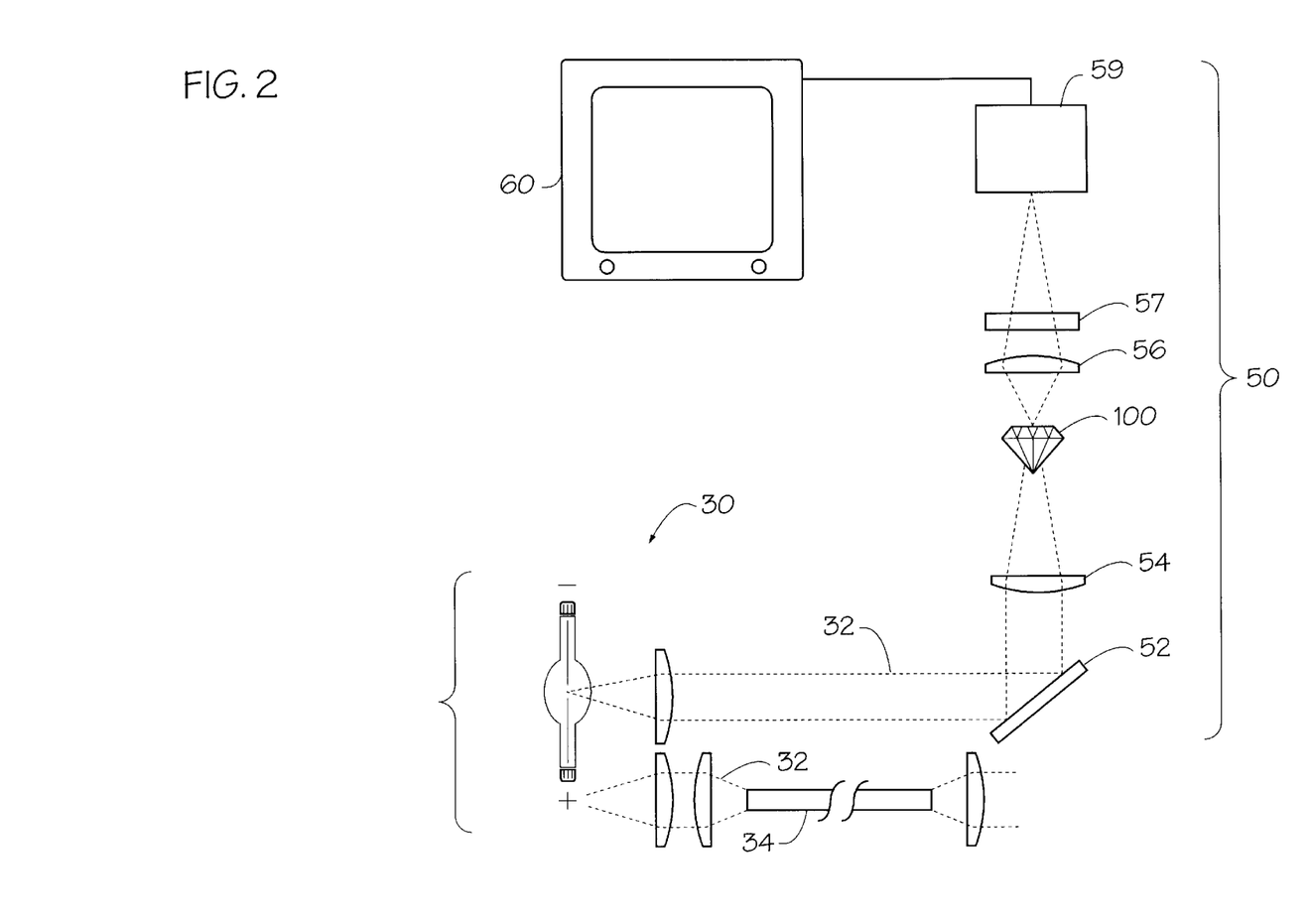
FIG. 2 is an overview of the technique of the invention illustrating an optical light path, and alternately, a fiber optical light path for illuminating the diamond.
Figure 3:
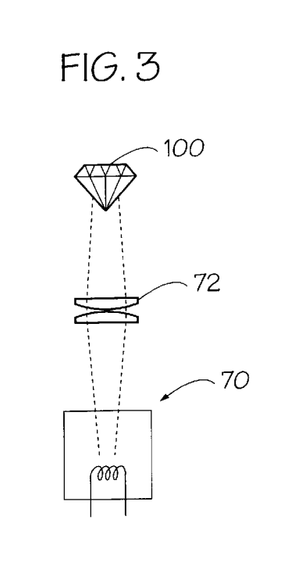
FIG. 3 illustrates a means for illuminating the diamond by an optical path, through a condenser stage.
Figure 4:
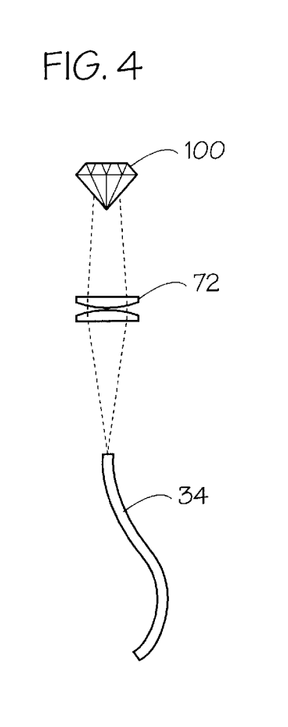
FIG. 4 illustrates a means for illuminating the diamond by a fiber optical path, through a condenser stage.
Figures 5, 6, 7:
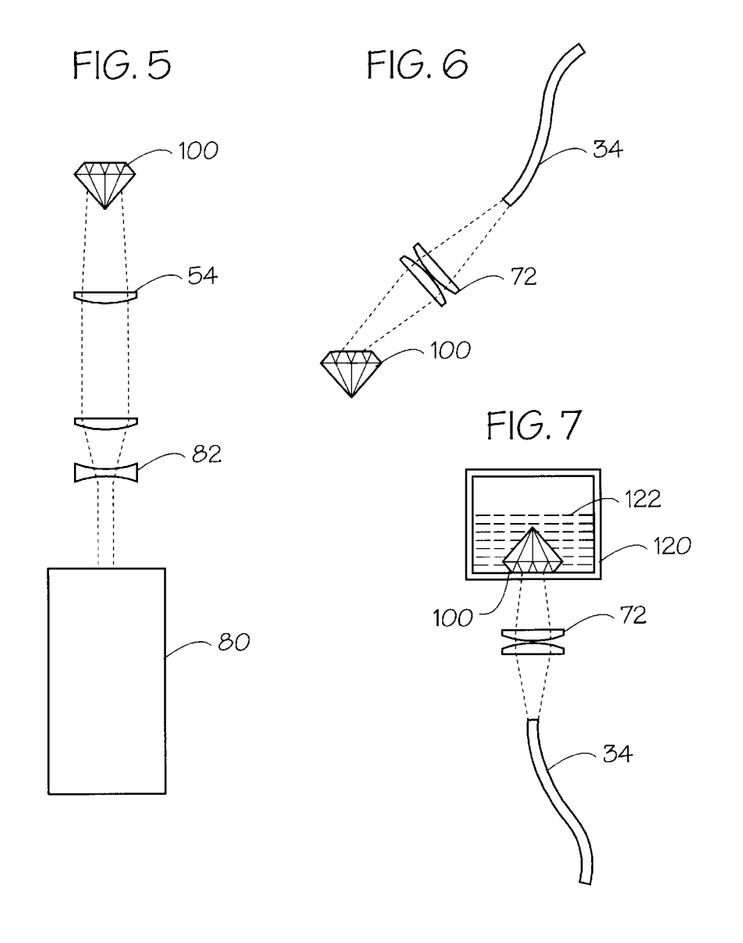
FIG. 5 illustrates a means for illuminating the diamond by a laser light source.
FIG. 6 illustrates a means for illuminating the top of the diamond.
FIG. 7 illustrates a means for illuminating the diamond in an immersion cell.

The preferred apparatus for detecting the presence of fracture filled portions 101 on and in a diamond 100, includes a means for producing 10 a beam 32 of ultra violet light radiation such shown in FIG. 1, including: an arc lamp power supply 20, a mercury arc lamp in housing 30, the light having a wavelength between 300 nm and 400 nm, a means for positioning the diamond 100 within the beam 32 so that the diamond 100 is irradiated by the beam 32. Such a positioning means might include a diamond holder 40 of any type well known to the diamond industry, and a means for observing 50 dark portions 101 on and in the diamond, such as a CCD camera sensitive to ultra violet light, used in conjunction with a video monitor 60. The dark portions 101 on and in the diamond correspond to the fracture filled portions on the diamond 100. FIG. 2 illustrates the components shown in FIG. 1 schematically. At the bottom of FIG. 2 is shown two alternative approaches to providing a light beam 32 to the observing means 50, namely, a free light beam directed from the light source 30 to the observing means 50 (shown above), and a fiber optical light path 34 (shown below). The observing means 50 includes, from bottom to top, in FIG. 2: a mirror 52, a condensing lens 54, the diamond 100, an objective lens 56, a filter 57 preferably centered on 365 nm, and a ultra violet charge coupled device (CCD) type camera 59. FIG. 3 illustrates an alternate method of illumination, namely a xenon flash lamp 70. FIG. 4 illustrates the use of a fiber optical cable 34 which could be used as shown to illuminate the diamond 100 directly, through a condenser lens set 72. FIG. 5 illustrates the use of a laser light source 80 for illumination, preferably through a beam expander 82. Notice that until this point we have described the illumination of a faceted diamond from the bottom only. It also is advantageous to illuminate the diamond 100 from the top surface, as shown in FIG. 6. FIG. 7 illustrates the use of an immersion cell 120 filled with a liquid 122 such as alfa mono bromonapthalene which is transparent to ultra violet light. This technique has been found to be beneficial in that the brightness of the light transmitted through the diamond 100 is enhanced.

Figure 8:
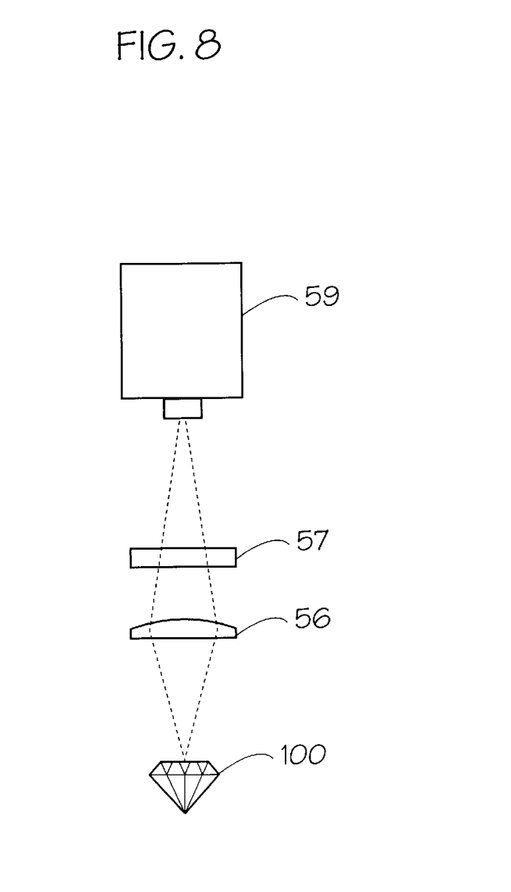
FIG. 8 illustrates a means for imaging the diamond by a vidicon camera.
Figure 9:
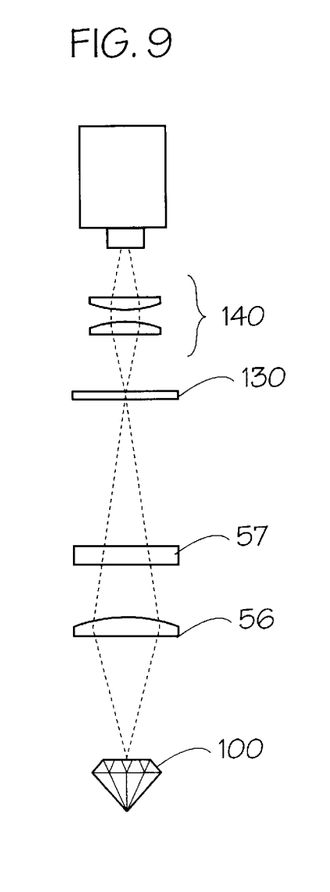
FIG. 9 illustrates a means for imaging the diamond by a CCD device through a fluorescent converter.
Figure 10:
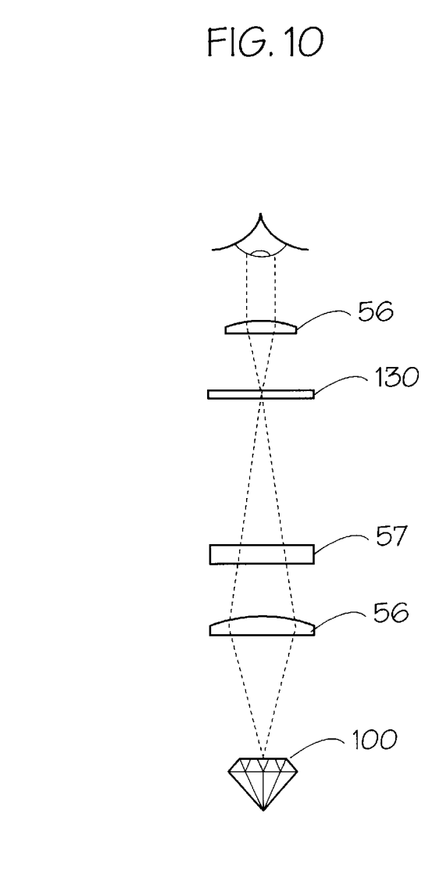
FIG. 10 illustrates a means for viewing the diamond through a fluorescent converter.

The observing means 50 preferably includes a means for magnification such as would be a function of the driver and expander electronic circuit (not shown separately) normally built into and made an integral part of most monitors 60. FIG. 8 illustrates the use of a ultra violet camera 59 for optical imaging. FIG. 9 illustrates the use of a visible light CCD camera used with relay lens set 140 and fluorescent converter 130, the later component being well known in the prior art for converting an ultra violet light beam to a visible light beam. FIG. 10 illustrates the method of direct visual observation. Various means for electro-optical imaging and image storage such as described above are possible embodiments in the present invention, but other known means for such are also within the scope and overall intent in the invention. In one embodiment, the observing means is positioned to receive the beam as reflected light from the diamond, while in a second embodiment, the observing means is positioned to receive the beam as light transmitted through the diamond. Either of these techniques may be employed while immersing the diamond, while in the beam, in a fluid that is transparent to the beam. As has been described above and shown in FIG. 7 immersion fluids 122 may be advantageously used for the improved imaging of both filled and unfilled fractures in gemstones. Immersion fluids, in the literature, date to the time of Sir Isaac Newton who introduced the concept of refraction of light. Mineralogists routinely approximate the refractive index of an unknown substance by comparing known and unknown substances immersed in fluids of known value. Such fluids are readily available with indexes ranging from 1.3 to 1.8 and higher. There are two liquids at the high end of the refractive index that are generally useful. One is a-monobromonaphthlene with an index of 1.65 and the other is methylene iodide with an index of 1.74. Of special interest is the use of high index immersion fluids for the inspection of high index cut gems such as diamond and others. Diamond is, of course, of particular interest in the gemstone industry worldwide. It has an index of 2.417. Unfortunately a-monobromonaphthlene's index is too low to be of interest for diamond analysis and methylene iodide is opaque in the near UV.

Optical dispersion manifests itself as the variation of refractive index of a substance with wavelength of the light. In the case of most materials such dispersion is uniform, but with a material having an energy absorption band, a large discontinuity in the dispersion occurs. The index of refraction on the short wavelength side of the absorption band falls. On the long wavelength side of the band the index rises abruptly and can reach values in the range of 2.35 for certain dyes over a narrow passband. This phenomenon is called anomalous dispersion and may be used in one embodiment of the present invention. It has been observed that the maximum of the index of refraction occurs at about the halfway point on the long wavelength side of the absorption band. This means that, in general, more than half of the incident light will be attenuated and lost to the absorption band. However, the remaining light is available for transmission. The index may remain at a high value over a range of 10 to 15 nm. Utilizing a combination of long and short band pass filters, or a narrow band interference filter centered on the high index region, the gemstone under investigation can be viewed by means of the UV microscope, CCD sensors and monitor as previously described. Dyes such as p-terphenyl, p-quaterphenyl, carbostyril 124, popop, and coumarin 152 having absorption bands at 276 nm, 298 nm, 349 nm, 358 nm, and 394 nm respectively may be employed in the present method. Solvents such as 1-chloronaphthaline, 1,2 dibromobenzene, 1-methylnaphthalene and 1-iodonaphthalene having indexes of 1.63, 1.61, 1.61 and 1.71 respectively may be combined with the dyes to enable the analysis of diamonds and other high index gemstones using the apparatus as shown in FIG. 7, the immersion cell 120, and FIG. 2 for imaging and visualization, as well as the methods herein described for anomalous dispersion wherein FIG. 11 shows a typical region of observation.

Figure 11:
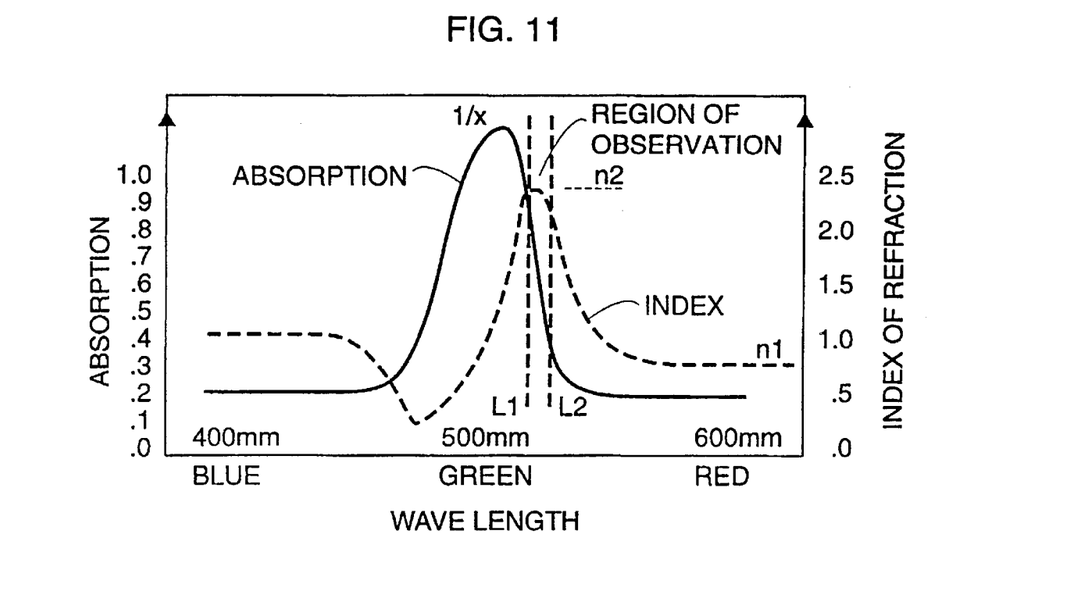
FIG. 11 illustrates a region of observation for the anomalous dispersion approach.

The apparatus has been described and shown above, the main improvement with the anomalous dispersion approach, as shown in FIG. 11, is that the fluid 122 has an index of refraction of say n1, the fluid having the characteristic of absorbing near-ultra-violet light energy over a specified bandwidth L1 to L2 so that at wavelengths near to, but greater than L1 the fluid exhibits anomalous dispersion and an index of refraction n2 much greater than n1, whereby observation of the fracture filled portions, in accordance with the previously described apparatus and method, is improved at the wavelengths of light just above L1.

Figure 12:
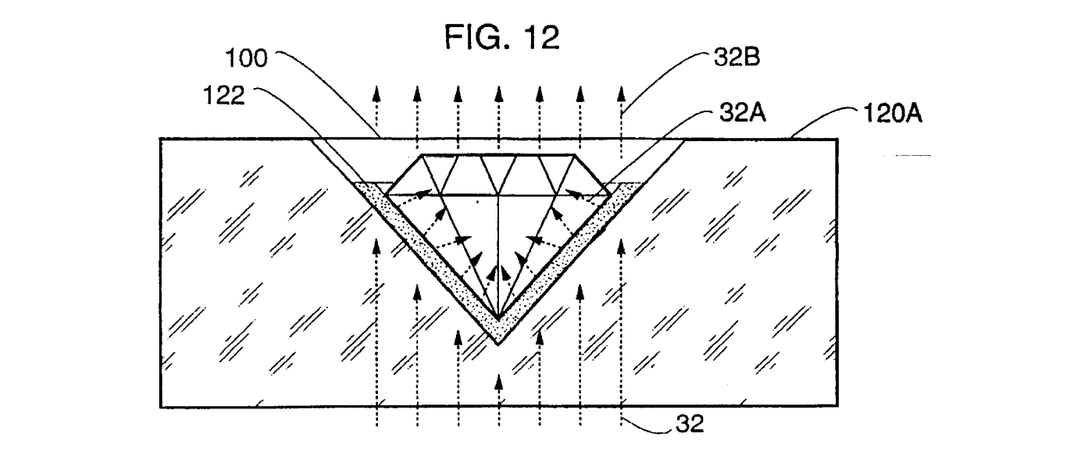
FIG. 12 illustrates a fixture for immersing a gemstone in a UV fluorescing fluid.

Ultra-violet fluorescence provides another embodiment in the present invention. In this embodiment the gemstone is at least partially immersed in a UV fluorescing material such as p-terphenyl which absorbs at 276 nm and fluoresces with a maximum at 354 nm. This region is sensitive to the detection of fracture filling materials used to treat diamonds and other gemstones. When the above dye is dissolved in an appropriate solvent it will flow around a gemstone placed in it, wetting its surface. This may be achieved by using the fixture shown in FIG. 12. The fixture may be made of fused silica and is formed or fabricated to provide a cavity with the same shape as the gemstone. A small amount of the dye-solvent fluid is placed into the cavity so that when the gemstone is pressed into the cavity a thin layer of the fluid flows around the base of the gemstone. The gemstone may also be fully immersed but this is less desirable since it attenuates light leaving at the top of the gemstone, i.e., as shown in FIG. 12 as reference 32B. The incoming short wavelength UV light 32 from below the gemstone travels through the fixture 120A and produces long wavelength fluorescence within the gemstone which is viewed from above with a UV microscope as shown in FIG. 1. A gemstone is generally cut to achieve total internal reflection (TIR). For diamonds the TIR is 41 degrees at each pavilion or a total included angle of 82 degrees. Using this approach is very effective, as all the light rays that enter the top surface of a diamond complete a two reflection round trip and emerge from the diamond without loss. For this discussion we have neglected the interfacial reflection from the entering rays and the interfacial reflection that occurs when the ray exit from the diamond. These reflections follow Fresnel's law. Dispersion takes place as the rays propagate through the diamond. All the efforts to make the diamond look beautiful optically tend to defeat efforts to examine it with transmitted light. When light rays arrive at the pavilion, they are effectively reflected away. This is the result of the TIR angle chosen for the facets. If the diamond were to be immersed in a liquid of matching index (2.41), the diamond would disappear in the fluid solution and the transmitted illumination would pass through unobstructed by any interfacial reflection created by the differences in the material mediums and their respective indexes of refraction. Currently no optically transparent liquid of the required index exists.

The UV fluorescence approach overcomes the index matching requirement by creating the source of illumination directly at the surface of the diamond as shown in FIG. 12. The dye solution 122, by wetting the surface of the diamond 100, allows UV excitation to cause fluorescent emission 32A directly at the diamond-fluid boundary. These light rays 32A pass into the diamond 100 providing a broad even illumination field useful for close examination of the internal structure of the diamond via exiting light 32B. In addition to the dyes mentioned, other substances have been found to provide useful results in the same way. Among these substances are sodium silicate solution, losoid grease and vacuum pump oil.

The apparatus as previously described and shown in FIG. 7 further may be modified to include a means for at least partial immersion 120A, in FIG. 12, of the gemstone 100, while in the beam 32, in a fluorescing fluid 122, the fluid fluorescing in response to the beam so as to illuminate the interior of the gemstone with fluorescent emission 32A, whereby observation from above, as shown in FIG. 1, of the fracture filled portions is improved.

The method of the present invention includes the following steps:
a) Producing a beam of ultra violet light radiation, with a wavelength of between 300 nm and 400 nm.
b) Positioning the diamond within the beam so that the diamond is irradiated by the beam.
c) Observing dark portions on and in the diamond which correspond to the fracture filled portions.

Additionally, the method of observation is preferably conducted through a means for magnification such as a microscope optical magnification stage. Also, the method may preferably be conducted through a means for electro-optical imaging and image storage, such as a vidicon camera and electro-optical imaging device such as a video monitor with a tape storage device.

Additionally, the method is preferably conducted through a means for fluorescent conversion of an ultra violet image, enabling direct visual observation. Further, the method may include the immersing of the diamond, while in the beam, in a fluid, the fluid being transparent to the beam. Such a step can significantly enhance the brightness of the image.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:
1. A method of detecting the presence of fracture filled portions on and in a gemstone comprising the steps of:
   a) producing a beam of ultra violet light radiation, the radiation having a wavelength of between 300 nm and 400 nm;
   b) positioning the gemstone within the beam so that the gemstone is irradiated by the beam;
   b' producing an image of the gemstone; and
   c) observing dark portions on and in the image of the gemstone; so that the dark portions on and in the image of the gemstone correspond to the fracture filled portions.

2. The method of claim 1 wherein step (c) is conducted through a means for magnification.

3. The method of claim 1 wherein step (b') is conducted through a means for electro-optical imaging and image storage.

4. The method of claim 1 wherein step (b') is conducted through a means for fluorescent conversion of an ultra violet image, enabling direct visual observation.

5. The method of claim 1 further including, after step (b), the further step of: immersing the gemstone, while in the beam, in a fluid, the fluid being transparent to the beam.

6. The method of claim 5 wherein step (c) is conducted through a means for magnification.

7. The method of claim 5 wherein step (b') is conducted through a means for electro-optical imaging and image storage.

8. The method of claim 5 wherein step (b') is conducted through a means for fluorescent conversion of an ultra violet image, enabling direct visual observation.

9. A apparatus for detecting the presence of fracture filled portions on and in a gemstone, comprising:
   a means for producing a beam of ultra violet light radiation, the radiation having a wavelength of between 300 nm and 400 nm;
   a means for positioning the gemstone within the beam so that the gemstone is irradiated by the beam;
   a means for imaging of light from the gemstone;
   a means for observing dark portions on and in the gemstone; so that the dark portions on and in the gemstone correspond to the fracture filled portions.

10. The apparatus of claim 9 wherein the observing means includes a means for magnification.

11. The apparatus of claim 9 wherein the imaging means includes a means for electro-optical imaging and image storage.

12. The apparatus of claim 9 wherein the imaging means includes a means for fluorescent conversion of an ultra violet image, enabling direct visual observation.

13. The apparatus of claim 9 wherein the beam producing means includes a condensing lens.

14. The apparatus of claim 9 wherein the beam producing means includes a fiber optic means for transmitting the beam.

15. The apparatus of claim 9 wherein the imaging means is positioned to receive the beam as reflected light from the gemstone.

16. The apparatus of claim 9 wherein the imaging means is positioned to receive the beam as light transmitted through the gemstone.

17. The apparatus of claim 9 further including a means for immersing the gemstone, while in the beam, in a fluid, the fluid being transparent to the beam.

18. The apparatus of claim 17 wherein the observing means includes a means for magnification.

19. The apparatus of claim 17 wherein the imaging means includes a means for electro-optical imaging and image storage.

20. The apparatus of claim 17 wherein the imaging means includes a means for fluorescent conversion of an ultra violet image, enabling direct visual observation.

21. The apparatus of claim 17 wherein the beam producing means includes a condensing lens.

22. The apparatus of claim 17 wherein the beam producing means includes a fiber optic means for transmitting the beam.

23. The apparatus of claim 17 wherein the imaging means is positioned to receive the beam as reflected light from the gemstone.

24. The apparatus of claim 17 wherein the imaging means is positioned to receive the beam as light transmitted through the gemstone.

25. The apparatus of claim 17 wherein the fluid has an index of refraction of n1, the fluid having the characteristic of absorbing near-ultra-violet light energy over a specified bandwidth L1 to L2 so that at wavelengths near to, but greater than L1 the fluid exhibits anomalous dispersion and an index of refraction much greater than n1, whereby observation of the fracture filled portions is improved.

26. The apparatus of claim 9 further including a means for at least partially immersing the gemstone, while in the beam, in a fluorescing fluid, the fluid fluorescing in response to the beam so as to illuminate the interior of the gemstone with fluorescent emission, whereby observation of the fracture filled portions is improved.

* * * * *